United States Patent [19]

Loncaric

[11] 4,137,773
[45] Feb. 6, 1979

[54] ANTI-ELECTROSTATIC SAMPLING METHOD

[75] Inventor: Rado G. Loncaric, Dallas, Tex.

[73] Assignee: Atlantic Richfield Company, Los Angeles, Calif.

[21] Appl. No.: 858,991

[22] Filed: Dec. 9, 1977

[51] Int. Cl.$^2$ ............................................. G01N 1/10
[52] U.S. Cl. .............................. 73/421 B; 73/422 R; 361/215
[58] Field of Search .......... 73/421 B, 421.5 R, 422 R, 73/421 R; 361/215; 137/154

[56] References Cited

U.S. PATENT DOCUMENTS

| | | | |
|---|---|---|---|
| 2,260,419 | 10/1941 | Wrightsman | 73/422 R |
| 2,284,560 | 5/1942 | Corneil | 73/422 R |
| 2,911,607 | 11/1959 | Booth | 361/215 |
| 2,953,147 | 9/1960 | Hornback | 361/215 |
| 3,956,921 | 5/1976 | Himes | 73/421.5 R |

Primary Examiner—S. Clement Swisher
Attorney, Agent, or Firm—M. David Folzenlogen

[57] ABSTRACT

When liquid petroleum samples are taken from petroleum producing and transporting equipment in cold, dry areas, for example, northern Alaska, there is a danger of electrostatic sparking and explosion of the flammable liquids being sampled. This hazard is reduced by gentle sampling techniques and cooling the sample. The liquid sample line is cooled and the flow rate of the petroleum liquid is prevented from exceeding 1 meter per second. In addition, the liquid is flowed upward in the sample container thereby preventing flashing, agitation, and higher flow rates. For added safety, the sample container or the container and sample line may be prefilled with a noncombustible fluid. The container may also be made of metal and connected by an electrical conductor directly or indirectly to the equipment being sampled.

4 Claims, 1 Drawing Figure

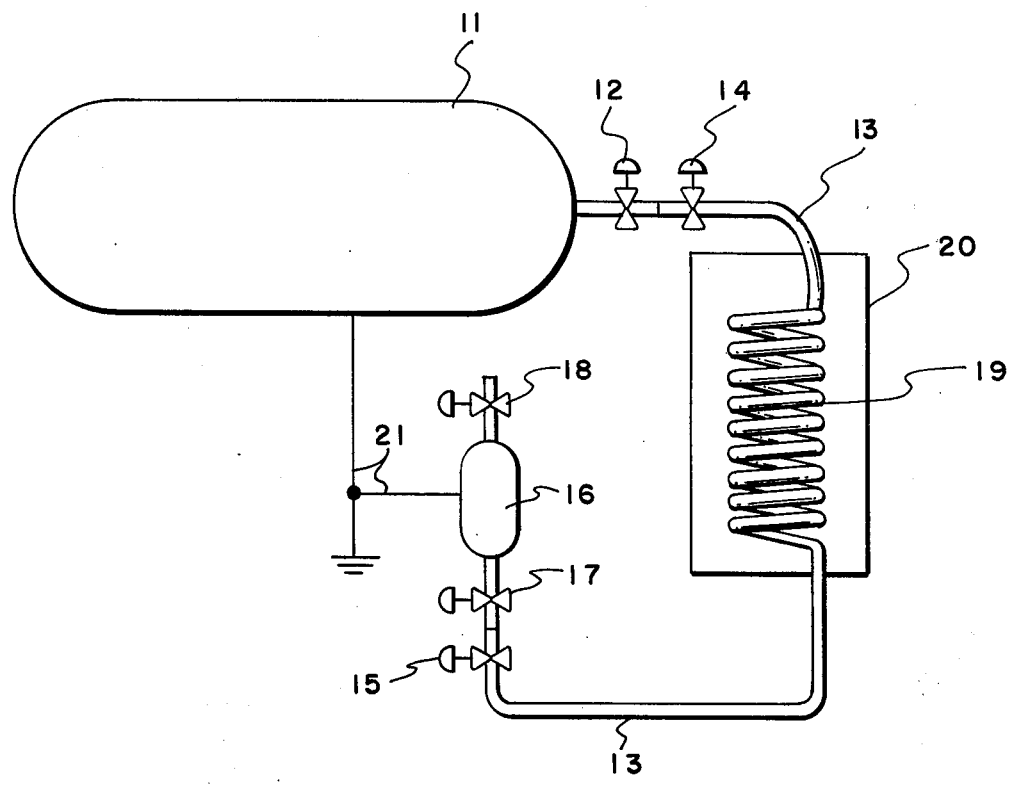

ANTI-ELECTROSTATIC SAMPLING METHOD

BACKGROUND OF THE INVENTION

This invention relates to a liquid sampling procedure for petroleum producing and transporting operation in areas where static electricity is a particular hazard.

When a petroleum liquid of low conductivity or mixed phases flows into and out of petroleum handling equipment, or is flowed through filters, screens or a valve, or is agitated, an electrostatic charge is built up in the liquid or on the inner walls of the equipment, screen, valve, or the like. This situation is aggravated by turbulence and flow velocity. The situation is especially severe in cold, dry crude oil producing areas, like those found in northern Alaska. When a sampling valve on such equipment is opened, the charge either present upon opening or generated by taking the sample may discharge creating a spark which sets off an explosion or fire.

SUMMARY OF THE INVENTION

Liquid petroleum samples are taken from operating equipment in at least three steps which combine to minimize the chances of an electrostatic produced spark. The liquid sample is flowed from the equipment to a sample container at low, nonturbulent rate, that is, less than 1 meter per second. The liquid sample is cooled as it passes to the sample container. The liquid is flowed upward in the container. For added control of the potential of sparks, the container or the sample container and line are prefilled with a noncombustible gas to eliminate oxygen. In addition, the sample container may be made of metal and grounded to the equipment by a metal electrical conductor. The conductor may be connected directly to the equipment or indirectly by way of a common ground.

BRIEF DESCRIPTION OF THE DRAWING

The drawing is a diagrammatical view illustrating the antistatic electricity sampling method of this invention.

DETAILED DESCRIPTION OF THE PREFERRED EMBODIMENT

Liquid petroleum samples, e.g., crude oil and topping distillates, are taken from operating, producing or transporting equipment in cold crude oil producing and handling areas like those found in northern Alaska. Such equipment includes flowlines, pipelines, tanks, treators, separators, pumps and the like. In the drawing, such equipment is depicted by tank 11. The sampling method involves at least three steps which combine to reduce the chances of electrostatic sparking and explosion or fire. For descriptive purposes, tank 11 is shown as having outlet valve 12. Outlet valve 12 may be in a building and connected to the equipment through a suitable manifold system. Connected to the outlet valve is sample line 13 which has end valves 14 and 15. End valve 15 is connected to sample container 16 which has sample valve 17 at its lower end and sample valve 18 at its upper end. Between end valves 14 and 15, sample line 13 is formed into coil 19 which is a simple form of heat exchanger. Surrounding coil 19 is sample cooler 20 which may be any sort of cooler, e.g., an ice or dry ice bath. The flow rate in sample line 13 may be controlled in any suitable way. It may also be metered if desired.

Preferably, the sample container will be made of metal and the container connected electrically, directly or indirectly, by way of ground line 21 to tank 11. Line 21 may be an electrical conductor directly connected to the tank, or line 21 may be connected to some other conductor, manifold line, pipeline, or equipment to which tank 11 is also connected. It is common practice to ground petroleum producing or handling equipment to a common piece of equipment or flowline.

In operation, petroleum liquid in tank 11 is flowed through valves 12 and 14 into sample line 13. The rate of flow of the petroleum liquid is controlled by one or more of the valves in the system so that the rate of flow in sample line 13 does not exceed 1 meter per second. This upper limit on the rate of flow takes into consideration the effects of flow rate on electrostatic charges, the physical characteristics of the sampling system, and the action of cooler 20.

The sample liquid enters cooler 20 and coil 19. In the cooler, the sample is kept cooler than it was in the tank. The cooled sample liquid flows out of cooler 20 to the lower end of sample container 16. It is important that the sample liquid be flowed into a low point of the sample container so that the sample liquid will flow upwardly as it enters and fills the sample container. This upward flow prevents excessive agitation and flow rate. If desired, both the sample line and the sample container may be cooled.

Preferably, sample line 13 or sample line 13 and sample container 16 will be prefilled with a noncombustion supporting gas that does not contaminate the sample, for example, nitrogen. As the sample is flowed into sample line 13 and then into the lower end of sample container 16, the sample liquid displaces some or all of the noncombustion supporting gas out the upper end of the sample container 18. Valve 17 may be connected to a suitable overflow container, not shown, to prevent accidental escape of flammable gases derived from the vapor pressure of the sample liquid.

The described sampling system is illustrative of the inventive concepts. The scope of the invention is not to be restricted to such embodiments. Various other arrangements and variations may be derived by one skilled in the art without departing from the spirit and scope of this invention.

The embodiments of the invention in which an exclusive property or privilege is claimed are defined as follows:

1. A method of taking liquid samples from petroleum handling equipment comprising flowing a liquid sample through a sample line at a rate of less than 1 meter per second, said sample line communicating with said equipment and with a sample container; cooling said liquid in at least a portion of said sample line, said portion between said equipment and said container, and flowing said liquid sample into a low point of said container so that said liquid sample flows upwardly in said container.

2. The method of claim 1 wherein the container is filled with a noncombustible fluid prior to starting flow of said liquid sample and the flowing liquid sample flows upwardly in said container and displaces at least a portion of the noncombustible fluid from said container at a high point of said container.

3. The method of claim 1 wherein the sample line and container are filled with a noncombustible fluid prior to starting flow of said liquid sample and the flowing liquid sample displaces at least a portion of said noncombustible fluid from said sample line and said container.

4. The method of claim 1 wherein the sample container is metallic and said container is connected to the petroleum handling equipment by an electrical conductor.

* * * * *